US00PP27551P3

(12) United States Plant Patent
Wood

(10) Patent No.: US PP27,551 P3
(45) Date of Patent: Jan. 17, 2017

(54) ***PHYSOCARPUS* PLANT NAMED 'SMPOMINI'**

(50) Latin Name: *Physocarpus opulifolius*
Varietal Denomination: SMPOMINI

(71) Applicant: Timothy D. Wood, Spring Lake, MI (US)

(72) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 95 days.

(21) Appl. No.: 14/545,046

(22) Filed: Mar. 19, 2015

(65) Prior Publication Data

US 2016/0278261 P1 Sep. 22, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — June Hwu
(74) *Attorney, Agent, or Firm* — C. A. Whealy

(57) ABSTRACT

A new and distinct cultivar of *Physocarpus* plant named 'SMPOMINI', characterized by its relatively compact, upright and uniform plant habit; vigorous growth habit; freely branching habit; dense and bushy habit; small dark green-colored leaves; inflorescences with numerous white to light pink-colored flowers; good garden performance; and resistance to Powdery Mildew.

2 Drawing Sheets

Botanical designation: *Physocarpus opulifolius*.
Cultivar denomination: 'SMPOMINI'.

BACKGROUND OF THE INVENTION

The present invention relates to a new and distinct *Physocarpus* plant, botanically known as *Physocarpus opulifolius* and hereinafter referred to by the name 'SMPOMINI'.

The new *Physocarpus* plant is a product of a controlled breeding program conducted by the Inventor in Grand Haven, Mich. The objective of the breeding program is to create new *Physocarpus* plants with smaller plant habit and unique flower forms.

The new *Physocarpus* plant originated from an open-pollination during the summer of 2006 in Grand Haven, Mich. of *Physocarpus opulifolius* 'Seward', disclosed in U.S. Plant Pat. No. 14,821, as the female, or seed, parent with an unknown selection of *Physocarpus opulifolius* as the male, or pollen, parent. The new *Physocarpus* plant was discovered and selected by the Inventor in 2008 as a single flowering plant within the progeny of the stated open-pollination in a controlled environment in Grand Haven, Mich.

Asexual reproduction of the new *Physocarpus* plant by softwood cuttings in a controlled environment in Grand Haven, Mich. since July, 2008 has shown that the unique features of this new *Physocarpus* plant are stable and reproduced true to type in successive generations of asexual reproduction.

SUMMARY OF THE INVENTION

Plants of the new *Physocarpus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMPOMINI'. These characteristics in combination distinguish 'SMPOMINI' as a new and distinct *Physocarpus* plant:

1. Relatively compact, upright and uniform plant habit.
2. Vigorous growth habit.
3. Freely branching habit; dense and bushy habit.
4. Small dark green-colored leaves.
5. Inflorescences with numerous white to light pink-colored flowers.
6. Good garden performance.
7. Resistance to Powdery Mildew.

Plants of the new *Physocarpus* can be compared to plants of the female parent, 'Seward'. Plants of the new *Physocarpus* differ from plants of 'Seward' in the following characteristics:

1. Plants of the new *Physocarpus* are more compact than plants of 'Seward'.
2. Plants of the new *Physocarpus* have smaller leaves than plants of 'Seward'.

Plants of the new *Physocarpus* can be compared to plants of the *Physocarpus* 'Donna May', U.S. Plant Pat. No. 22,634 also known as 'Little Devil'. In side-by-side comparisons conducted in Grand Haven, Mich., plants of the new *Physocarpus* differed from plants of 'Little Devil' in the following characteristics:

1. Plants of the new *Physocarpus* were more compact than plants of 'Little Devil'.
2. Plants of the new *Physocarpus* and 'Little Devil' differed in leaf color as plants of 'Little Devil' had brownish burgundy-colored leaves during the spring.
3. Plants of the new *Physocarpus* were more resistant to Powdery Mildew than plants of 'Little Devil'.

BRIEF DESCRIPTION OF THE PHOTOGRAPHS

The accompanying colored photographs illustrate the overall appearance of the new *Physocarpus* showing the colors as true as it is reasonably possible to obtain in colored reproductions of this type. Colors in the photographs may differ slightly from the color values cited in the detailed botanical description which accurately describe the colors of the new *Physocarpus*.

The photograph on the first sheet is a side perspective view of typical plants of 'SMPOMINI' grown in an outdoor nursery.

The photograph on the second sheet is a close-up view of a typical plant of 'SMPOMINI'.

DETAILED BOTANICAL DESCRIPTION

The aforementioned photographs and following observations, measurements and values describe plants grown during the early autumn in ground beds in an outdoor nursery in Grand Haven, Mich. and under cultural practices typical of commercial *Physocarpus* production. During the production of the plants, day temperatures ranged from 18° C. to 27° C. and night temperatures ranged from ranged from 5° C. to 10° C. Plants were two years old when the photographs and the description were taken. In the description, color references are made to The Royal Horticultural Society Colour Chart, 1995 Edition, except where general terms of ordinary dictionary significance are used.

Botanical classification: *Physocarpus opulifolius* 'SMPOMINI'.

Parentage:

*Female, or seed, parent.*—*Physocarpus opulifolius* 'Seward', disclosed in U.S. Plant Pat. No. 14,821.

*Male, or pollen, parent.*—Unknown selection of *Physocarpus opulifolius*, not patented.

Propagation:

*Type.*—By softwood cuttings.

*Time to initiate roots, summer.*—About 25 days at temperatures about 24° C.

*Time to produce a rooted young plant, summer.*—About two months at temperatures about 24° C.

*Root description.*—Fine to thick; white and brown in color.

*Rooting habit.*—Freely branching; dense.

Plant description:

*Plant and growth habit.*—Perennial shrub; relatively compact, upright and uniform plant habit; vigorous growth habit.

*Branching habit.*—Freely branching habit with about 50 lateral branches developing per plant; pinching enhances lateral branch development.

*Plant height.*—About 60 cm.

*Plant diameter* (*area of spread*).—About 56 cm.

Lateral branch description:

*Length.*—About 42 cm.

*Diameter.*—About 3 mm.

*Internode length.*—About 1.7 cm.

*Texture.*—Smooth, glabrous.

*Aspect.*—Erect to about 20° from vertical.

*Color.*—Close to 178A.

Leaf description:

*Arrangement.*—Alternate, simple.

*Length.*—About 4 cm.

*Width.*—About 2.5 cm.

*Shape.*—Cordate, tri-lobed.

*Apex.*—Acute.

*Base.*—Rounded to obtuse.

*Margin.*—Lobed, serrulate.

*Texture, upper and lower surfaces.*—Smooth, glabrous.

*Venation pattern.*—Pinnate.

*Color.*—Developing leaves, upper surface: Close to 136A. Developing leaves, lower surface: Close to 138B. Fully expanded leaves, upper surface: Close to 139A tinted with close to 178A; autumn color, close to 183A; venation, same as lamina. Fully expanded leaves, lower surface: Close to 138B; venation, close to 138B.

*Petioles.*—Length: About 1.5 cm. Diameter: About 1 mm. Texture, upper and lower surfaces: Smooth, glabrous. Color, upper and lower surfaces: Close to 176A.

Flower description:

*Flower appearance and arrangement.*—Single rotate flowers arranged in terminal and axillary corymbs; corymbs roughly spherical in shape; freely flowering habit with usually about 24 flowers per inflorescence; flowers face upright to outwardly.

*Flower longevity.*—Flowers last for about three to four weeks on the plant; flowers not persistent.

*Natural flowering season.*—Plants flower from May though June in Michigan.

*Fragrance.*—None detected.

*Inflorescence height.*—About 2 cm.

*Inflorescence diameter.*—About 2 cm.

*Flower diameter.*—About 5 mm.

*Flower length* (*height*).—About 4 mm.

*Flower buds.*—Length: About 3 mm. Diameter: About 3 mm. Shape: Rounded. Color: Close to 57D.

*Petals.*—Quantity and arrangement: Five petals in a single whorl. Length: About 3 mm. Width: About 3 mm. Shape: Elliptic to obovate. Apex: Obtuse. Margin: Entire. Texture, upper and lower surfaces: Smooth, glabrous. Color: When opening, upper and lower surfaces: Close to 155D and 58D. Fully opened, upper and lower surfaces: Close to 155D and 58D.

*Sepals.*—Quantity and arrangement: Five in a single whorl. Length: About 3 mm. Width: About 2.5 mm. Shape: Broadly subulate. Apex: Acute. Margin: Entire. Texture, upper and lower surfaces: Smooth, glabrous. Color: When opening, upper and lower surfaces: Close to 144A. Fully opened, upper and lower surfaces: Close to 144A.

*Peduncles.*—Length: About 1.5 cm. Diameter: About 2 mm. Strength: Moderately strong. Texture: Smooth, glabrous. Color: Close to 144A.

*Pedicels.*—Length: About 2 mm. Diameter: About 1 mm. Strength: Moderately strong. Texture: Smooth, glabrous. Color: Close to 144A.

*Reproductive organs.*—Androecium: Quantity per flower: About 30. Anther length: About 0.5 mm. Anther shape: Oblong. Anther color: Close to 58A. Amount of pollen: Scarce. Pollen color: Close to 58A. Gynoecium: Quantity per flower: About three to four. Pistil length: About 0.5 mm. Style length: About 0.5 mm. Style color: Close to 145D. Stigma appearance: Globular. Stigma color: Close to 145D. Ovary color: Close to 145D.

*Seeds and fruits.*—Seed and fruit development have not been observed on plants of the new *Physocarpus* plant.

Garden performance: Plants of the new *Physocarpus* have been observed to have good garden performance and to tolerate rain, wind and temperatures ranging from about −25° C. to about 35° C.

Pathogen & pest resistance: Plants of the new *Physocarpus* have been observed to be resistant to Powdery Mildew. Plants of the new *Physocarpus* have not been shown to be resistant to pests and other pathogens common to *Physocarpus* plants.

It is claimed:

1. A new and distinct *Physocarpus* plant named 'SMPO-MINI' as illustrated and described.

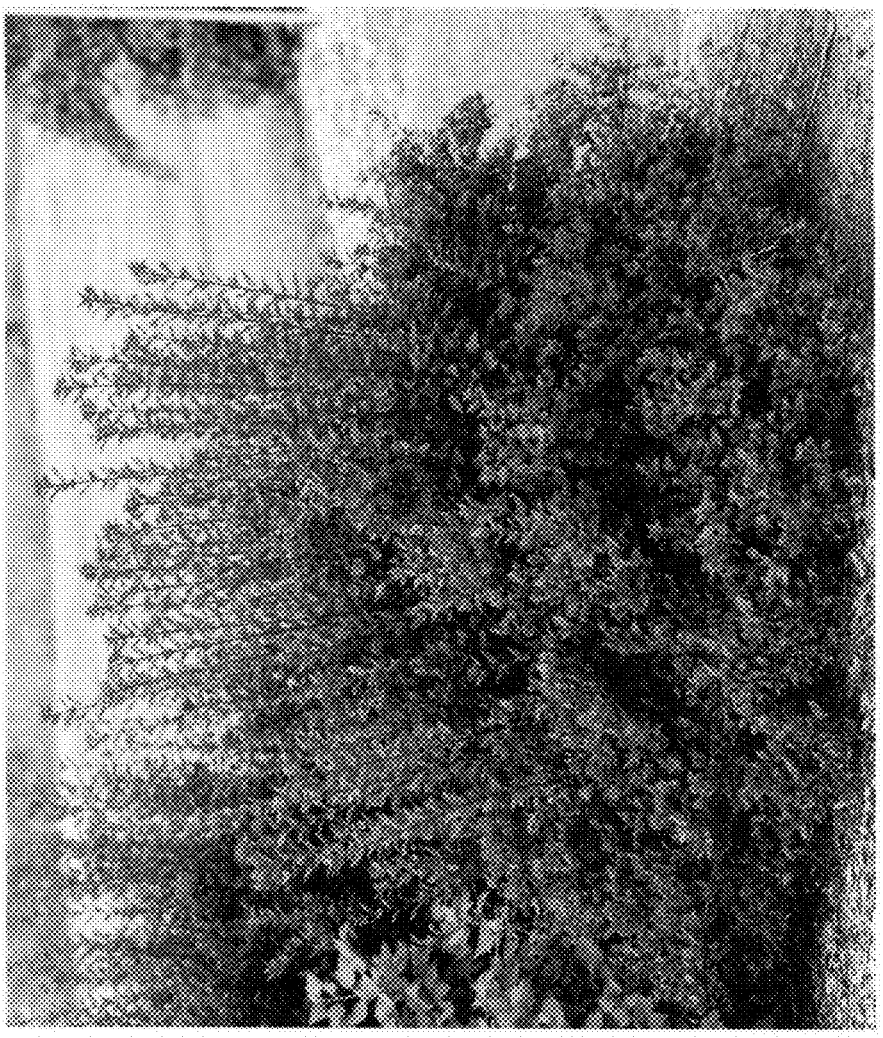

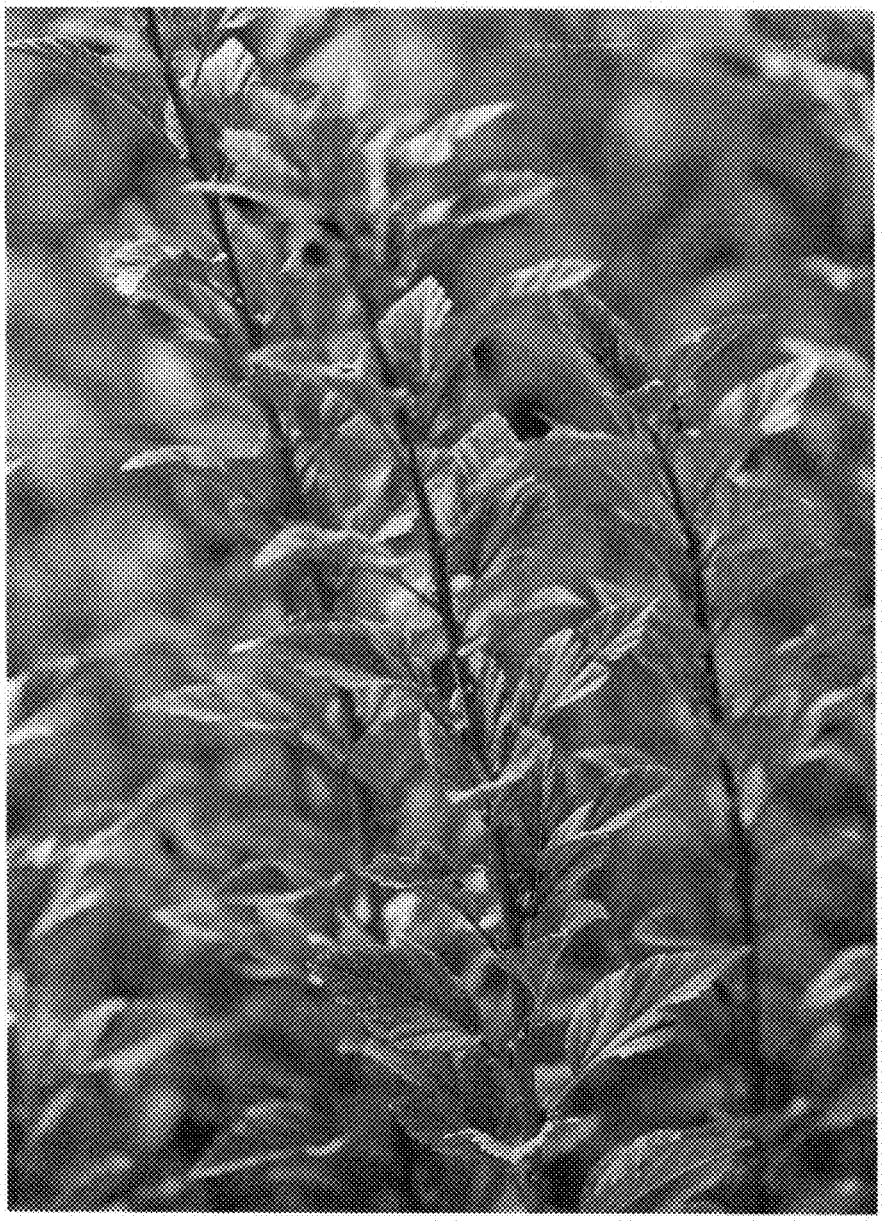

* * * * *